United States Patent
Bernhardt et al.

(10) Patent No.: US 7,660,390 B2
(45) Date of Patent: Feb. 9, 2010

(54) X-RAY DIAGNOSTICS METHOD AND DEVICE

(75) Inventors: Philipp Bernhardt, Forchheim (DE); Klaus Klingenbeck-Regn, Nürnberg (DE); Michael Maschke, Lonnerstadt (DE)

(73) Assignee: Siemens Aktiengesellschaft, Munich (DE)

(*) Notice: Subject to any disclaimer, the term of this patent is extended or adjusted under 35 U.S.C. 154(b) by 487 days.

(21) Appl. No.: 11/165,100

(22) Filed: Jun. 23, 2005

(65) Prior Publication Data

US 2005/0286681 A1    Dec. 29, 2005

(30) Foreign Application Priority Data

Jun. 25, 2004   (DE)   ........................ 10 2004 030 833

(51) Int. Cl.
*H05G 1/64*    (2006.01)
(52) U.S. Cl. ....................... 378/98.8; 378/116
(58) Field of Classification Search .................... 378/63, 378/98.8, 116, 207
See application file for complete search history.

(56) References Cited

U.S. PATENT DOCUMENTS

| | | | | |
|---|---|---|---|---|
| 3,783,282 A | * | 1/1974 | Hoppenstein | ................ 378/41 |
| 4,985,908 A | | 1/1991 | Asahina | |
| 5,319,696 A | * | 6/1994 | Abdel-Malek et al. | ...... 378/108 |
| 5,838,325 A | * | 11/1998 | Deen et al. | ................... 715/841 |
| 6,222,907 B1 | | 4/2001 | Gordon, III et al. | |
| 6,233,310 B1 | * | 5/2001 | Relihan et al. | .............. 378/108 |
| 6,333,964 B1 | * | 12/2001 | Hobel | ........................ 378/98.7 |
| 2003/0048935 A1 | * | 3/2003 | Keren | ......................... 382/130 |
| 2003/0095626 A1 | * | 5/2003 | Anderton | .................... 378/98.7 |
| 2003/0097062 A1 | * | 5/2003 | Toth et al. | .................... 600/425 |
| 2004/0062341 A1 | * | 4/2004 | Popescu et al. | ................. 378/4 |
| 2005/0069083 A1 | * | 3/2005 | Klingenbeck-Regn | ........ 378/62 |
| 2007/0071172 A1 | * | 3/2007 | Mollus et al. | ............... 378/108 |

FOREIGN PATENT DOCUMENTS

| | | |
|---|---|---|
| DE | 3619863 A1 | 12/1986 |
| DE | 69429489 12 | 4/1995 |
| DE | 199 19 423 A1 | 11/2000 |
| EP | 1 322 143 A2 | 6/2003 |

* cited by examiner

*Primary Examiner*—Edward J Glick
*Assistant Examiner*—Mona M Sanei

(57) ABSTRACT

An x-ray diagnostics method is specified, in particular for use in angiography and cardiology, by means of which a particularly good image quality can be achieved in an easily manageable manner for the patient (P) and the medical personnel, at the same time as a comparatively low radiation exposure. Furthermore, a specific x-ray device (1) for implementing the method comprising an x-ray emitter (2), an x-ray detector (3) and a control unit (10) is specified to control the x-ray emitter (2). In this way the control unit (10) is allocated an operating element (15), by means of which a control parameter (S) characterizing the image quality, the detector input dose or the contrast noise ratio can be continuously varied, as a function of which a number of recording parameters (U,I,t,F) are set by means of the control device (10).

9 Claims, 1 Drawing Sheet

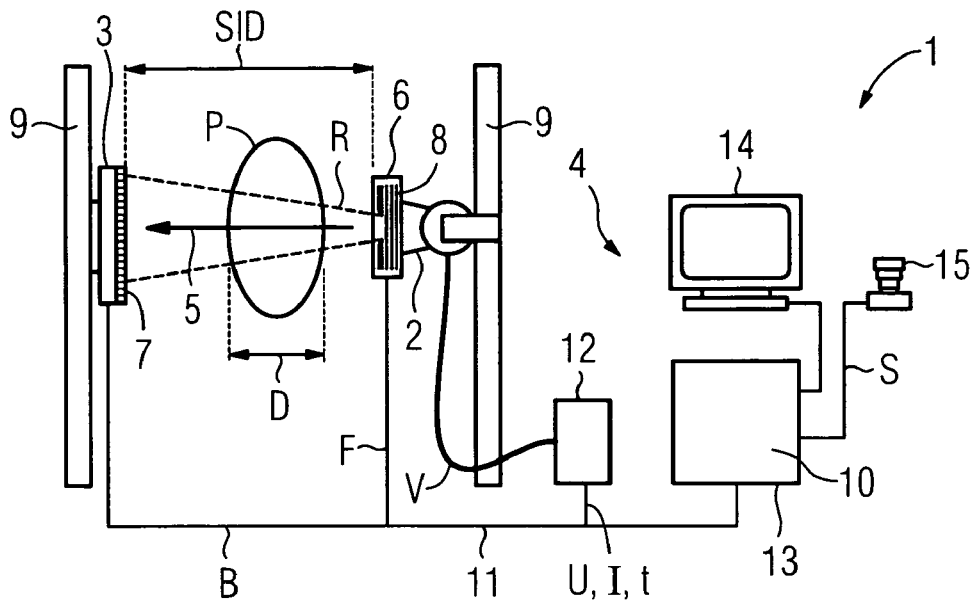
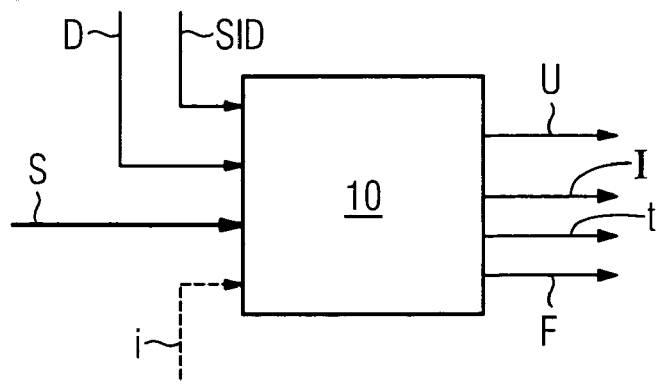
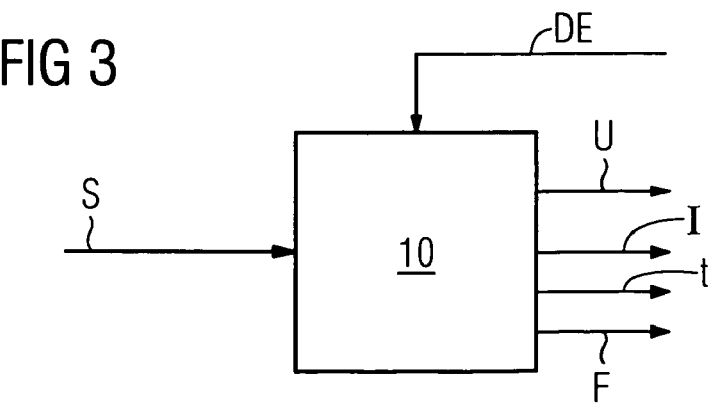

X-RAY DIAGNOSTICS METHOD AND DEVICE

CROSS REFERENCE TO RELATED APPLICATIONS

This application claims priority to the German application No. 10 2004 030 833.0, filed Jun. 25, 2004 which is incorporated by reference herein in its entirety.

FIELD OF INVENTION

The invention relates to an x-ray diagnostics method (in particular a digital method) and an X-ray device, especially for use in angiography and cardiology.

BACKGROUND OF INVENTION

A method of this type and a device associated therewith are known from DE 199 19 423 A1. In particular the mAs product can hereby be adjusted as a control variable which is definitive for the image quality. In the course of the known method, operating parameters such as tube current and scan time are varied such that unreliable operating states are avoided without significantly reducing the mAs product and thus the image quality.

With x-ray examinations in angiography and cardiology an outstanding image quality is of particular significance in order to be able to clearly distinguish between the comparatively weakly absorbent bodily structures examined here, in particular tissue and vessels, and if necessary catheters and stents. At the same time, however, it must be ensured that the patient and the medical staff are exposed to the smallest possible x-ray dose.

SUMMARY OF INVENTION

It is thus usual to operate a generic x-ray device in two operating modes, namely fluoroscopy and acquisition. In this way, in the course of the fluoroscopy with preparatory steps using comparatively small x-ray doses, e.g. the position of the patient in the desired exposure position, the selection of a specific recording segment or the selection of specific recording parameters are carried out. The actual recording of the x-ray image used for diagnosis purposes subsequently takes place in the course of the acquisition with comparatively high radiation intensity on the other hand.

A method of this-type is known for example from EP 1 322 143 A2. For both operating modes, the tube current is adjusted as a function of the tube voltage on the basis of a controlling curve assigned in each instance, with which the controlling curve is modified in accordance with the method such that a predetermined maximum input dose is not exceeded when radiation is applied to an object.

Furthermore, methods are known for example from U.S. Pat. No. 6,222,907 B1 or U.S. Pat. No. 6,233,310 B1, in which the image quality of an x-ray recording or the detector input dose are controlled or regulated, in which as a function of the depth of the transilluminated body tissue (or how fat the patient is) and as a function of the distance between the x-ray emitter and the detector of the x-ray device, said distance being referred to as SID (source image distance), predefined recording parameters, in particular the tube voltage (kV), tube current (mA), exposure time (ms) as well as the setting of an x-ray filter preceding the x-ray emitter are set such that a constant image quality and/or detector input dose is achieved with the smallest possible patient dose.

An object of the invention is to specify an x-ray diagnostic method particularly suited to use in angiography and cardiology, by means of which a particularly good image quality can be achieved in an easily manageable manner at the same time as particularly low x-ray exposure for the patient and the medical personnel. Furthermore, the object of the invention is further to specify an x-ray device particularly suited to implementing the method.

The object is achieved by the claims. Accordingly, a control parameter is provided which is linked to a number of recording parameters such that it functions as a gauge for the image quality, the detector input dose or the contrast noise ratio. The control parameter can thus be continuously varied, so that the image quality, the detector input dose and/or the contrast noise ratio can be directly and continuously adjusted by means of varying the control parameter. The control parameter is linked to the recording parameters optionally by specifying a set of functional dependencies, in other words mathematical functions, characteristic fields, etc, by means of which each recording parameter is assigned a value dependent on the value of the control parameter, while the control parameter is optionally provided in the course of control as a target value of the detector input dose or of the contrast noise ratio.

As a result of the facilities for continuous adjustment according to the invention, an attending doctor who considers it expedient to adapt the image quality and/or detector input dose can quickly and directly do so by activating an individual operating element. In accordance with the method, the recording parameters linked to the control parameter are automatically adjusted in the background such that the increase or reduction in the image quality, the detector input dose and/or the contrast noise ratio predetermined by the control parameter is implemented. The attending doctor is thereby able to set an image quality at any time during an x-ray examination which is sufficiently good to satisfy the current requirements. On the other hand, the doctor is able to restrict the image quality at any time to the level required at that time, thereby simultaneously minimizing the radiation exposure for the patient and him/herself.

Tube voltage, tube current, exposure time, and/or the adjustment of an x-ray filter, in particular the filter thickness are preferably considered as recording parameters. In an advantageous embodiment of the method, the recording parameters are not only controlled as a function of the control parameter but also as a function of at least one further input variable. How fat the patient is, the SID, and/or an image enlargement factor are thereby preferably considered here as input variables.

Provision is advantageously made in that the control parameter can be varied at any point during the x-ray examination, in other words particularly also during an exposure phase, so that the attending doctor is also able to match the recording conditions to the current requirements during the image recording. This prevents doctors from making wrong diagnoses as a result of image quality problems and having to amend or even discontinue their treatment. Furthermore, the doctor thus has direct control over patient dosage and can significantly reduce this at any time by foregoing above-average image quality.

In an advantageous embodiment of the invention, provision is made that several alternative sets of functional dependencies are provided in order to link the control parameter with the recording parameters, from which the attending doctor can make his/her selection. In this way, the definition of various objects or structures to be examined, e.g. iodine as a contrast medium, vessels, stents, etc., is particularly enabled, in relation to which the image quality is optionally optimized. By way of example, a corresponding set of functional dependencies can be selected that depicts stents in a particularly contrasting manner etc.

In terms of the x-ray device, the object is achieved according to the invention by the features of claim 8. The device accordingly comprises an x-ray emitter, a digital x-ray detector and a control unit for controlling the x-ray emitter. The control unit is here assigned an operating element, by means of which the control unit can be assigned a continuously adjustable control parameter, as a function of which the control unit adjusts a number of recording parameters whilst implementing the method described above.

The operating element is preferably designed as a joystick, foot pedal, rotary knob or rotary wheel or as a trackball. A virtual operating element can nevertheless be provided instead of a physical operating element, said virtual operating element being implemented within a graphic user interface of an operating software.

BRIEF DESCRIPTION OF THE DRAWINGS

Exemplary embodiments of the invention are described below with reference to a drawing, in which:

FIG. 1 shows a schematic representation of an x-ray device with an x-ray emitter, an x-ray detector, a control unit and a control element assigned to one of these, FIG. 2 shows the control unit of the device according to FIG. 1 in a schematic flow diagram, and FIG. 3 shows a modified design of the control unit in a representation according to FIG. 2

DETAILED DESCRIPTION OF INVENTION

Components and variables corresponding to one another are always provided with the same reference characters in all the figures.

The X-ray device 1 represented schematically in FIG. 1 comprises an X-ray emitter 2, a digital x-ray detector (abbreviated below as detector) 3 and a control and evaluation system 4. A multileaf collimator 6 and a scattered ray raster 7 are interposed in the direction of radiation 5 between the x-ray emitter 2 and the detector 3.

The multileaf collimator 6 also serves to cut out a partial beam of a desired variable from the x-ray radiation R generated by the x-ray emitter 2, which falls on the detector 3 through a patient P to be examined or an object to be examined and the scattered ray raster 7. The multileaf collimator 6 additionally contains a filter arrangement 8, by means of which the x-ray radiation R generated by the x-ray emitter 2 can be diminished and/or can be modified in terms of its spectral distribution. The filter arrangement 8 can be adjusted particularly in terms of its filter thickness F (FIG. 2).

The scattered ray raster 7 serves to mask out scattered radiation hitting the detector 3 at a low angle and which would corrupt an x-ray image B recorded by the detector 3.

The x-ray emitter 2 and the detector 3 are fixed to a stand 9 in an adjustable manner, or above or below an examination table.

The control and evaluation system 4 comprises a control unit 10 for controlling the x-ray emitter 2 and/or the detector 3. To control the x-ray emitter 2, the control unit 10 is linked to an x-ray generator 12 by means of a data line 11, said x-ray generator generating an electrical supply voltage V for radiation generation and outputting this to the x-ray emitter 2. The voltage rate (subsequently referred to as tube voltage U) and the current strength (subsequently referred to as tube current I) of the supply voltage V are set together with the exposure time t by means of the control unit 10 and are given to the x-ray generator 12 as a recording parameter. In a similar manner, the control unit 10 adjusts the filter thickness F and is given to the depth parameter as a recording parameter.

The control unit 10 is a software component of a data processing system 13, which preferably comprises further software components for preparing and evaluating x-ray images B, which are generated by the detector 3 and transmitted to the data processing system 13 by way of the data line 11.

The data processing system 13 is linked to peripheral devices 14, such as a screen and a keyboard for example for the purpose of inputting and outputting data. The data processing system 13 is additionally linked to an operating element 15, which is preferably designed as a joystick and by means of which the control unit 10 is given a control parameter S for adjusting the image quality or the detector input dose.

FIG. 2 shows a schematic representation of a first embodiment of the control unit 10 and the variables supplied thereto and/or output therefrom. The display shows that the control unit 10 is fed, in addition to the control parameter S, the distance SID between the x-ray emitter 2 and the detector 3 and how fat the patient is D, in other words the depth of the transilluminated tissue of the patient P, as input variables. The output variables of the control unit 10 are, as already mentioned, the tube voltage U, the tube current I, the exposure time t and the filter thickness F.

The control parameter S is a signal, the rate of which can be adjusted b y the attending doctor by actuating the operating element 15 continuously at any time within predetermined limits, e.g. between 0 and 1. The adjustability of the control parameter S is thus also understood as 'continuous', if the control parameter S, particularly with digital information processing, comprises a multiplicity of discrete, narrowly distanced adjustment facilities. The adjusted value of the control parameter S is shown on the screen 14, so that the attending doctor is able to read off his current settings at all times.

In the control unit 10, a corresponding function dependency U (S,D,SID), I(S,D,SID), t(S,D,SID) and F(S,D,SID) is deposited for each recording parameter U,I,F,t, by means of which a value dependent on the rate of the control parameter S and the further input variables D, SID is assigned to the corresponding recording parameter U, I, t and/or F. The functional dependencies U(S,D,SID), I(S,D,SID), t(S,D,SID) and F(S,D,SID) are deposited in the form of mathematical model functions or in the form of supporting defined characteristic fields. The functional dependencies U(S,D,SID), I(S,D,SID), t(S,D,SID) and F(S,D,SID) are thus selected such that with the variation of the control parameter S between its minimum value and its maximum value, the set of recording parameters U, I, t, F output is varied such that the image quality of a recorded x-ray image is varied correspondingly between a minimum state and a maximum state. In this way, the control parameter S represents a direct gauge for the image quality. The respective ratio of the recording parameters U,I,t,F with a predetermined value of the input variables S,D,SID is thus selected such that the patient dose is minimized with a constant image quality. The form of the functional dependencies U(S,D,SID), I(S,D,SID), t(S,D,SID) and F(S,D,SID) is to be determined from the empirical series of tests on the x-ray device 1, by means of model calculations.

Optionally several alternative sets of functional dependencies $U_i(S,D,SID)$, $I_i(S,D,SID)$ $t_i(S,D,SID)$ and $F_i(S,D,SID)$ are deposited in the control unit 10, in which i=1,2,3, . . .

represents the number of the set to be selected. The control unit 10 defines this number 1 for the selection of a specific set of functional dependencies.

This method allows several alternative definitions of the image quality to be available for selection, e.g. to allow a specific object to be examined or a specific structure to come to light in a particularly clear manner. By way of example, provision is made that a first set $U_1(S,D,SID)$, $I_1(S,D,SID)$, $t_1(S,D,SID)$ and $F_1(S,D,SID)$ of functional dependencies is optimized for the representation of iodine as the contrast medium used. A second set of functional dependencies $U_2(S,D,SID)$, $I_2(S,D,SID)$, $t_2(S,D,SID)$ and $F_2(S,D,SID)$ represents for instance a form of the image quality optimized for the representation of stents.

In a modification of the control unit 10 represented in FIG. 3, the control parameter S is not considered as a gauge for the image quality, but as a gauge for the detector input dose, which represents an objectively measurable variable in contrast to the image quality. In this embodiment, the control unit 10 is designed as a closed-loop control and acquires the continuously measured value of the detector input dose DE as an actual value, which is compared with the control parameter S as a target value for the purpose of carrying out a target/actual value comparison. If the measured detector input dose DE falls short of the rate of the control parameter S, the recording parameters U, I, t, F are controlled such that the detector input dose DE is accordingly increased. The detector input dose DE is similarly lowered by a corresponding control of the recording parameters U, I, t, F, if the measured detector input dose DE exceeds the control parameter S. The respective ratio of the recording parameters U, I, t, F is in turn determined based on deposited characteristics such that the patient dose is always minimized with a given detector input dose DE.

In place of the detector input dose DE, a further modification of the control unit 10 (not shown in more detail) provides for the contrast noise ratio to be considered as a control variable. Furthermore, the two variants of the control unit 10 shown in FIGS. 2 and 3 can also be simultaneously implemented for the selection with the same x-ray device 1, so that the attending doctor can select whether the operating element 15 can be used to control the image quality, the detector input dose, or, if necessary, the contrast noise ratio. Optionally, the settings of image processing software are automatically adjusted as a function of the control parameter S. By way of example, setting a low detector input dose allows for stronger low pass filtering to be set than in the case of a high detector input dose.

In place of a joystick, further possible embodiments of the operating element 15 are alternatively provided, in particular a foot pedal functioning in a similar manner to a gas pedal, a rotary knob or a rotary wheel with the possibility of a positive or negative deflection, as well as a trackball.

The invention claimed is:

1. An X-ray diagnostics method, comprising:
    examining a patient by operating an X-ray device; and
    adjusting a control parameter representing an image quality, a detector input dose, or a contrast noise ratio for enhancing the image quality of the X-ray device between a predetermined minimum and maximum value;
    wherein said adjusting a control parameter is effective to correspondingly adjust a plurality of recording parameters according to a pre-determined functional dependency between the plurality of recording parameters and the control parameter such that a present value of the recording parameters is adjusted based upon a present value of the control parameter according to the pre-determined functional dependency;
    wherein the control parameter is adjusted by actuating an operating element assigned to the control parameter:
    wherein the X-ray device is configured to have the image quality adjusted using the operating element at any point in time during the examination of the patient; and
    wherein a plurality of alternative pre-determined functional dependencies of at least one of the plurality of recording parameters from the control parameter is provided such that a current value of the at least one of the plurality of recording parameters is set based upon a current value of the control parameter according to one of the plurality of alternative pre-determined functional dependencies selected by a user of the x-ray device.

2. The method according to claim 1, wherein the X-ray diagnostics method is related to angiography or cardiology.

3. The X-ray diagnostics method according to claim 1, wherein the plurality of recording parameters include a voltage of an X-ray tube of the X-ray device, a current an X-ray tube, an exposure time, or a filter setting.

4. The X-ray diagnostics method according to claim 1, wherein at least one of the plurality of recording parameters is adjusted based upon an input variable chosen from the group consisting of a thickness of the patient, a distance between an X-ray tube and an X-ray detector of the X-ray device, and an enlargement factor.

5. The X-ray diagnostics method according to claim 1, wherein the control parameter is adjusted during an exposure phase while an X-ray image is recorded.

6. The X-ray diagnostic method according to claim 1, wherein the control parameters is a measured value of the detector input dose or the contrast noise ratio, and wherein at least one of the plurality of recording parameters is adjusted based on the control parameter.

7. An X-ray device for examining a patient, comprising:
    an X-ray emitter;
    an X-ray detector;
    a control unit for controlling the X-ray emitter, the control unit adapted to adjust a control parameter representing an image quality, a detector input dose, or a contrast noise ratio for enhancing the image quality of the X-ray device; and
    an operating element for receiving a user input regarding the control parameter;
    wherein the control unit is further adapted to correspondingly adjust a plurality of recording parameters according to a pre-determined functional dependency between the plurality of recording parameters and the control parameter such that a present value of the recording parameters is adjusted based upon a present value of the control parameter according to the pre-determined functional dependency;
    wherein the X-ray device is configured to have the imaging quality adjusted using the operating element at any point in time during the examination of the patient; and
    wherein a plurality of alternative pre-determined functional dependencies of at least one of the plurality of recording parameters from the control parameter is provided such that a current value of the at least one of the plurality of recording parameters is set based upon a current value of the control parameter according to one of the plurality of alternative pre-determined functional dependencies selected by a user of the x-ray device.

8. The X-ray device according to claim 7, wherein the operating element is a joystick, a foot pedal, a rotary knob, a rotary wheel or a trackball.

9. The X-ray diagnostic method according to claim 1, wherein the control parameter is a target detector input dose, and further comprising:

acquiring an actual detector input dose during said examining of the patient;

comparing the target detector input dose to the actual detector input dose;

if the actual detector input dose is less than the target detector input dose, adjusting the plurality of recording parameters to increase the actual detector input dose in a subsequent examination of the patient; and if the actual detector input dose is more than the target detector input dose, adjusting the plurality of recording parameters to decrease the actual detector input dose in a subsequent examination of the patient.

* * * * *

UNITED STATES PATENT AND TRADEMARK OFFICE
CERTIFICATE OF CORRECTION

PATENT NO. : 7,660,390 B2  Page 1 of 1
APPLICATION NO. : 11/165100
DATED : February 9, 2010
INVENTOR(S) : Bernhardt et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 559 days.

Signed and Sealed this

Thirtieth Day of November, 2010

David J. Kappos
*Director of the United States Patent and Trademark Office*